(12) United States Patent
Jess et al.

(10) Patent No.: US 8,730,601 B2
(45) Date of Patent: May 20, 2014

(54) FLUORESCENCE OBSERVATION SYSTEM AND SET OF FILTERS

(75) Inventors: Helge Jess, Oberkochen (DE); Roland Guckler, Aalen-Dewangen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/205,847

(22) Filed: Aug. 9, 2011

(65) Prior Publication Data
US 2012/0300294 A1    Nov. 29, 2012

Related U.S. Application Data

(60) Provisional application No. 61/371,885, filed on Aug. 9, 2010.

(30) Foreign Application Priority Data

Aug. 9, 2010    (DE) .......................... 10 2010 033 825

(51) Int. Cl.
*G02B 21/06* (2006.01)
*G02B 5/22* (2006.01)

(52) U.S. Cl.
USPC .......................................... 359/885; 359/385

(58) Field of Classification Search
USPC .......................................... 359/358, 385, 885
See application file for complete search history.

(56) References Cited

U.S. PATENT DOCUMENTS

| | | | |
|---|---|---|---|
| 5,647,368 A | 7/1997 | Zeng et al. | |
| 6,212,425 B1 | 4/2001 | Irion et al. | |
| 6,667,830 B1 | 12/2003 | Iketaki et al. | |
| 6,899,675 B2 | 5/2005 | Cline et al. | |
| 2001/0046050 A1* | 11/2001 | Hoyt | 356/417 |
| 2003/0227674 A1* | 12/2003 | Nihoshi et al. | 359/386 |
| 2006/0227319 A1* | 10/2006 | Imura | 356/256 |
| 2007/0165235 A1 | 7/2007 | Haridas | |
| 2009/0234234 A1* | 9/2009 | Machida | 600/476 |
| 2010/0044583 A1 | 2/2010 | Steffen et al. | |

FOREIGN PATENT DOCUMENTS

| | | |
|---|---|---|
| DE | 195 48 913 A1 | 7/1997 |
| DE | 199 80 759 T1 | 10/2001 |
| DE | 102 01 005 B4 | 10/2003 |
| DE | 697 35 174 T2 | 2/2006 |
| DE | 10 2006 015 272 A1 | 10/2007 |
| DE | 10 2008 034 008 A1 | 1/2010 |
| EP | 0 802 413 A2 | 10/1997 |
| WO | WO 2005/051182 A1 | 6/2005 |

OTHER PUBLICATIONS

Tsou et al., "Human Vision and Color," Dec. 13, 2007, Taylor and Francis, Encyclopedia of Optical Engineering, 748-759.*
Office Action in the corresponding German Application No. 10 2010 033 825.7, dated Jan. 12, 2011, 8 pages.

* cited by examiner

*Primary Examiner* — Alicia M Harrington
*Assistant Examiner* — Marin Pichler
(74) *Attorney, Agent, or Firm* — Potomac Patent Group PLLC

(57) ABSTRACT

A fluorescence observation system, a method for performing a fluorescence observation, and a set of filters that can be used in such system and method are provided.

8 Claims, 3 Drawing Sheets

FLUORESCENCE OBSERVATION SYSTEM AND SET OF FILTERS

CROSS-REFERENCES TO RELATED APPLICATIONS

This application claims priority to U.S. Provisional Patent Application No. 61/371,885, filed on Aug. 9, 2010 and German Patent Application No. 10 2010 033 825.7, filed on Aug. 9, 2010, the disclosures of which are hereby incorporated by reference in their entirety for all purposes.

FIELD OF THE INVENTION

The present invention relates to a fluorescence observation system, a method for performing a fluorescence observation and a set of filters which can be used in such system and method.

BACKGROUND OF THE INVENTION

Fluorescence observation is used in many fields of engineering, biology and medicine in order to visibly discriminate between different structures of an object. Herein, an illumination light filter is disposed in a beam path between an illumination light source and an object to be observed, wherein the illumination light filter allows substantially only light to traverse the filter which can excite a fluorescence of a fluorescent dye. An observation light filter is disposed in a beam path of imaging optics, wherein the observation light filter allows only fluorescent light to traverse the filter whereas light which can traverse the illumination light is substantially not allowed to traverse the observation light filter. Fluorescent structures of the object can be perceived as bright regions in an image which is observed with the eye by viewing into the observation optics or which is recorded by a camera via the observation optics, and non-fluorescing structures of the object remain dark such that structures contained in the non-fluorescing regions cannot be perceived.

It is desirable that also non-fluorescent regions of the object can be seen in the image in order to be able to better determine a position of fluorescent structures relative to the non-fluorescent structures. In this respect, U.S. Pat. No. 6,212,425 B1 suggests to adjust transmission characteristics of the illumination light filter and of the observation light filter relative to each other such that both the fluorescent structures of the object emitting the fluorescent light and non-fluorescent structures reflecting light are visible downstream of the observation light filter.

It has been found that non-fluorescent regions of an object are not satisfactorily visible with such adjustment of the illumination light filter and the observation light filter.

SUMMARY OF THE INVENTION

Accordingly, it is desirable to provide a set of filters, a fluorescence observation system and a method for performing a fluorescence observation allowing to better perceive non-fluorescent regions of an object.

The present invention has been accomplished taking the above problems into consideration.

The present invention provides sets of filters, fluorescence observation systems and methods allowing to observe fluorescent and non-fluorescent regions of an object.

According to embodiments, an illumination light filter has a transmission characteristic depending on the wavelength of the light which is a sum of a first partial characteristic and a second partial characteristic, wherein the first partial characteristic has a first wavelength range at wavelength below a threshold wavelength in which the transmission has values greater than a first value, and wherein the second partial characteristic has a second wavelength range at wavelengths above the threshold wavelength, in which the transmission has values less than a second value and greater than a third value, wherein the transmission of the illumination light filter has values less than a fourth value at wavelengths between the first wavelength range and the second wavelength range.

The threshold wavelength is a wavelength determined based on a used fluorescence process and separates wavelengths used for exciting the fluorescence process from wavelengths used for detecting the fluorescence process. In certain embodiments, the threshold wavelength is selected such that it is greater than a maximum of the excitation spectrum of the used fluorescence process and less than a maximum of an emission spectrum of the used fluorescence process. It is, however, possible to deviate from such selection, and the threshold wavelength can be selected to be less than the wavelength of the maximum of the excitation spectrum or greater than the wavelength of the maximum of the excitation spectrum, since excitation and emission spectra of fluorescence processes overlap in practice.

The first partial characteristic of the transmission characteristic of the illumination light filter has a function of supplying fluorescence excitation light to the object. For this purpose, the first partial characteristic has, in the first wavelength range below the threshold wavelength, values of transmission which are greater than the first value, wherein the first value is selected to be as high as possible when designing the filter. Exemplary values are greater than 0.75 or 0.9. A value of 1.0 can be a target for optimization, wherein such value can be only approximately reached in practice.

The second partial characteristic of the transmission characteristic of the illumination light filter has a function of supplying a certain amount of light to the object which is not used for exciting the fluorescence but for making non-fluorescent structures of the object visible. Since this light has wavelengths above the threshold wavelength, it can traverse the observation light filter when it is reflected by the object such that non-fluorescent structures of the object can be perceived due to such light.

Since fluorescent light generated by a fluorescent object typically has a low intensity, it is desirable that an intensity with which non-fluorescent regions of the object can be perceived in the fluorescent image is not substantially greater than the intensity with which the fluorescent regions are perceived since the fluorescent regions are otherwise outshined by the non-fluorescent regions. For that reason, it may be advantageous that the amount of light supplied to the object via the second partial characteristic is limited by selecting the transmission of the illumination light filter in the second wavelength range to be smaller than the second value and greater than the third value. Herein, the second value is less than the first value, such that the maximum transmission in the second wavelength range is significantly less than the maximum transmission in the first wavelength range. However, the maximum transmission in the second wavelength range is greater than the third value, wherein the third value represents a significant transmission rather than a transmission which is very small and which is present in wavelength ranges of the transmission characteristic of the filter in which the filter should preferably transmit no light at all. Such low transmission values are provided, for example, between the first wavelength range and the second wavelength range where the transmission is less than the fourth value, wherein the fourth value represents a transmission of the filter such that the filter transmits preferably no light at all at these wavelengths.

Summarized, the illumination light filter may have the following properties: the filter transmits a significant amount of light of plural wavelength ranges which are separated from each other, wherein at least one of the plural wavelength ranges is located below the threshold wavelength and allows a large amount of light to traverse, whereas at least one of the plural wavelength ranges is located above the threshold wavelength and allows to traverse a relatively low but still significant amount of light.

According to certain embodiments, the first value can be 0.50 and/or the second value can be 0.01, the third value can be 0.0005 and/or the fourth value can be 0.0002.

According to some embodiments, the observation light filter may have a transmission characteristic which is a sum of a third partial characteristic and a fourth partial characteristic. However, the fourth partial characteristic is optional, such that the transmission characteristic of the observation light filter can be completely represented by a characteristic which is illustrated in more detail as the third partial characteristic below.

The third partial characteristic has at least one wavelength range at wavelengths above the threshold wavelength in which the transmission has values which are greater than the first value. The third partial characteristic has a function of allowing both the fluorescent light and that light which serves to perceive the non-fluorescent regions to traverse the filter. The light which serves to perceive the non-fluorescent regions was allowed to reach the object due to the second partial characteristic of the illumination light filter, for example. Since intensities of fluorescent light are typically low, maximum values of the transmission in the third wavelength range are as high as possible. For example, such maximum values are greater than the first value illustrated above. As a result, both fluorescent structures of the object and non-fluorescent structures of the object can be perceived. This is achieved by supplying a significant amount of light having wavelengths such that it does not necessarily excite the fluorescence is supplied to the object and allowed to traverse the observation light filter together with the fluorescence light.

Such property may be represented by the following formulas:

$$0 \le \frac{1}{300 \text{ nm}} \int_{400 \text{ nm}}^{700 \text{ nm}} T_1(\lambda) \cdot T_3(\lambda) \cdot d\lambda < A_1 \text{ and} \quad (1)$$

$$2A_1 < \frac{1}{300 \text{ nm}} \int_{400 \text{ nm}}^{700 \text{ nm}} T_L(\lambda) \cdot T_O(\lambda) \cdot d\lambda < A_2; \quad (2)$$

wherein:
$\lambda$ designates the wavelength,
$T_1(\lambda)$ is the first partial characteristic,
$T_2(\lambda)$ is the second partial characteristic,
$T_3(\lambda)$ is the third partial characteristic,
$T_L(\lambda) = T_1(\lambda) + T_2(\lambda)$ is the transmission characteristic of the illumination light filter,
$T_O(\lambda)$ is the transmission characteristic of the observation light filter, and
$A_1, A_2$ are numbers between 0 and 1.

Formula (1) shows that a spectral overlap between the first partial characteristic of the illumination light filter for supplying fluorescence excitation light to the object and the third partial characteristic of the observation light filter for allowing fluorescence light to traverse may have a value $A_1$.

Formula (2) shows that a significant amount of light which is not fluorescence light and may thus be used to observe non-fluorescent regions of the object may traverse the combination of the illumination light filter and the observation light filter.

According to certain embodiments, $A_2$ can be 0.1, or $A_2$ can be 0.05, or $A_2$ can be 0.01, or $A_2$ can be 0.005.

In embodiments in which the transmission characteristic of the observation light filter is the sum of the third partial characteristic and the fourth partial characteristic, the fourth partial characteristic has, at wavelength below the threshold wavelength, a fourth wavelength range in which the transmission has values which are less than the second value and greater than the third value. The fourth partial characteristic has a function of allowing light to traverse the filter which is not fluorescence light and which may thus be used to perceive non-fluorescent objects. Since this light should not outshine the fluorescences, the amount of light which can traverse the observation light filter due to the fourth partial characteristic is limited by selecting maximum values of the transmission in the fourth wavelength range such that they are smaller than the second value which is significantly smaller than the first value which may represent a transmission optimized for maximal transmission. On the other hand, the amount transmitted by the observation light filter below the threshold wavelength should still be significant. For that reason, the maximum value of the transmission in the fourth wavelength range is greater than the third value which is significantly greater than the fourth value which represents a transmission which is intended to substantially prevent transmission.

With such arrangement, there is provided light for observing non-fluorescent regions of the object from at least two different wavelength ranges, mainly the light which is not fluorescence light and which is supplied to the object due to the second partial characteristic of the illumination light filter and which traverses the observation light filter due to the third partial characteristic, and light which is supplied to the object due to the first partial characteristic of the illumination light filter and which traverses the observation light filter due to the fourth partial characteristic. These two wavelength ranges for observing non-fluorescent regions of the object have a spectral distance from each other. This spectral distance achieves an advantage in that the non-fluorescent regions do not appear monochromatic. Moreover, non-fluorescent regions can be perceived in plural spectral ranges, resulting in that different structures in the non-fluorescent regions of the object can be better perceived as compared to a monochromatic perception.

Herein, it is possible that the second partial characteristic of the illumination light filter and the fourth partial characteristic of the observation light filter allow the transmission of light in plural spectral ranges which are separated from each other. These spectral ranges can be selected such that the light available for the observation of non-fluorescent regions originates from plural spectral ranges which can be selected such that a mixture of the light is nearly white light. A non-fluorescent white surface can be perceived as a white surface through the system of the illumination light filter and the observation light filter, accordingly.

According to some embodiments, a set of filters comprises an illumination light filter and an observation light filter. A transmission characteristic of the observation light filter has, at wavelength below a threshold wavelength, at least one wavelength range in which a transmission has values which are greater than a first value, and the transmission characteristic of the illumination light filter has, at wavelength above the threshold wavelength, at least one wavelength range in which the transmission has values which are less than a fourth value. A transmission characteristic of the observation light filter has, at wavelength above the threshold wavelength, at least one wavelength range in which the transmission has values greater than the first value, and the transmission characteristic of the observation light filter has, below the threshold wavelength, at least one wavelength range in which the transmission has values which are smaller than the fourth value;
wherein $$2A_1 < \frac{1}{300 \text{ nm}} \int_{400nm}^{700nm} T_L(\lambda) \cdot T_O(\lambda) \cdot d\lambda < A_2, \quad (2)$$

$$\frac{\int_S T_L(\vec{r}) \cdot T_O(\vec{r}) \cdot \vec{r} \cdot dr}{\int_S T_L(\vec{r}) \cdot T_O(\vec{r}) \cdot dr} = \vec{R} \text{ and} \quad (3)$$

$$|\vec{W} - \vec{R}| \leq 0,2; \quad (4)$$

wherein:
λ designates the wavelength,
$T_L(\lambda)$ is the transmission characteristic of the illumination light filter,
$T_O(\lambda)$ is the transmission characteristic of the observation light filter,
$A_1, A_2$ are numbers between 0 and 1,
$\vec{r}$ is a coordinate in the CIE xy chromaticity diagram of the CIE 1931 XYZ color space,
S is a line called the spectral locus in the CIE xy chromaticity diagram of the CIE 1931 XYZ color space, and
$\vec{W}$ is the white point in the CIE xy chromaticity diagram of the CIE 1931 XYZ color space.

As already illustrated above, formula (2) shows that a significant amount of light which is not fluorescence light and which may serve for observing non-fluorescent regions of the object may traverse the combination of the illumination light filter and the observation light filter.

Formula (3) shows that the light which traverses the combination of the illumination light filter and the observation light filter and which is not fluorescence light belongs to different spectral ranges and that its spectral intensities are adjusted such that its mixture is nearly white light.

For defining these properties, reference is made to the CIE 1931 XYZ color space. This color space has a chromaticity diagram in which a red portion of a light is represented by the coordinate x and the green portion of light is represented by the coordinate y, wherein a blue portion z of the light fulfils x+y+z=1. A horseshoe-shaped curved line called the spectral locus of the CIE-chromaticity diagram represents the pure spectral colors. The white point has the coordinates x=1/3, y=1/3.

The integrals of the formula (3) are calculated along the line S which is the spectral locus line in the in the CIE xy chromaticity diagram of the CIE 1931 XYZ color space. Formula (3) represents a determination of a center of gravity of the light intensities on the spectral locus line, wherein a weighting is performed with the product $T_L \cdot T_O$ which represents the transmission through the combination of the illumination light filter and the observation light filter. The result of the determination of the center of gravity is the vector $\vec{R}$ in the CIE xy chromaticity diagram of the CIE 1931 XYZ color space.

Formula (4) shows that a distance between the result $\vec{R}$ of the determination of the center of gravity and the white point $\vec{W}$ in the CIE xy chromaticity diagram of the CIE 1931 XYZ color space is less than a predetermined value and is, thus, close to the white color.

According to further embodiments, the sets of filters illustrated above are integrated with a fluorescence observation system comprising a light source for illuminating the object. Herein, the transmission characteristics of the filters can be adjusted such that a spectrum of the light generated by the light source is taken into account. For example, this can be achieved by replacing the product $T_L \cdot T_O$ in the above formulas by a product $I_Q \cdot T_L \cdot T_O$, wherein $I_Q$ represents the spectral distribution of the light of the light source.

BRIEF DESCRIPTION OF THE DRAWINGS

The forgoing as well as other advantageous features of the disclosure will be more apparent from the following detailed description of exemplary embodiments of the disclosure with reference to the accompanying drawings. It is noted that not all possible embodiments of the present disclosure necessarily exhibit each and every, or any, of the advantages identified herein.

DETAILED DESCRIPTION OF THE INVENTION

Figure 1:
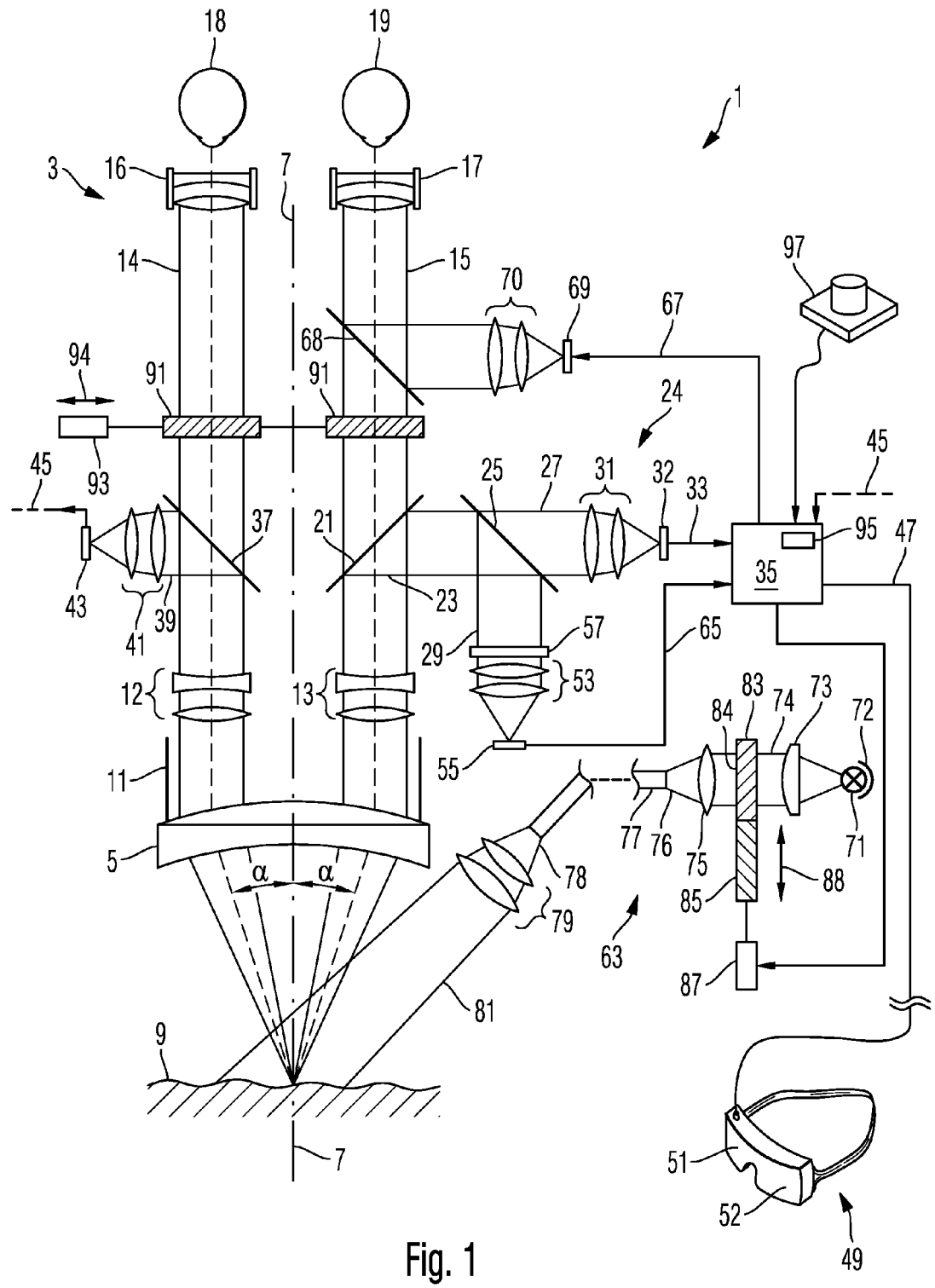
FIG. 1 is a schematic illustration of a fluorescence observation system.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

An embodiment of a fluorescence observation system is illustrated with reference to a surgical microscope below. However, embodiments of the fluorescence observation system are not limited to surgical microscopes and comprise any type of fluorescence observation system in which illumination light directed to an object is filtered with an illumination light filter and in which light emerging from the object is filtered with an observation light filter.

Referring to FIG. 1, a fluorescence observation system or microscope 1 comprises microscopy optics 3 including an objective lens 5 having an optical axis 7. An object 9 to be observed is located in an object plane of the objective lens 5. Light emerging from the object 9 is formed into an image side beam 11 by the objective lens 5, wherein two zoom systems 12, 13 are located in the beam 11 and spaced apart from the optical axis 7. The zoom systems 12, 13 select two partial beams 14 and 15 from the beam 11 and supply the partial beams 14, 15 to oculars 16, 17 via deflecting prisms (not shown). A user looks into the oculars with his left eye 18 and right eye 19 in order to perceive a magnified representation of the object 9.

A semi-transparent mirror 21 may be located in the partial beam 15 in order to supply a portion of the light as a beam 23 to a camera system 24. The camera system 24 may comprise one camera or plural cameras. In the illustrated embodiment, the camera system 24 comprises a camera 32 receiving light of the beam 23 having traversed a semi-transparent mirror 25 via camera adapter optics 31, and a camera 55 receiving light of the beam 23 reflected from the semi-transparent mirror 25 via a filter 57 and camera adapter optics 53. The filter 57 can be a fluorescence light filter which transmits only fluorescence light of a fluorescent dye contained in the object 9. Thus, the camera 32 can detect a normal light image of the object 9, whereas the camera 55 can detect a fluorescence light image of the object 9. Images of the cameras 32 and 55 are supplied to a controller 35 via data connections 33 and 65, respectively, and can be stored in a memory 95 of the controller.

Similarly, a semi-transparent mirror 37 can be located in the other partial beam 14 in order to reflect a partial beam 39 which is supplied to a camera 43 via camera adapter optics 41 such that the camera 43 may also detect a normal light image, wherein detected images of the camera 43 are transmitted to the controller 35 via a data connection 45.

A display 69 is connected to the controller 35 via a data connection 67, and an image displayed on the display 69 is projected into the beam path of the ocular 17 via projection optics 70 and a further semi-transparent mirror 68 located in the partial beam 15, such that the user may directly perceive both the image displayed on the display 69 and the image of the object with his eye 19. The controller 35 may, for example, project data or images of the object detected by the cameras 32, 55 and 43, or generated by an analysis of the detected images.

The controller 35 may also supply the images detected by the cameras to a head mounted display 49, wherein the head mounted display includes two displays 51, 52 for the right and left eyes, respectively, of the user.

The microscope 1 further comprises an illumination system 63 for generating an illumination light beam 81 directed to the object 9. For this purpose, the illumination system 63 comprises a broad band light source, such as, for example, a halogen lamp or a Xenon lamp 71, a reflector 72 and a collimator 73 for generating a collimated light beam 74 which may be directed onto an entrance end 76 of a fiber bundle 77 by one or more lenses 75, in order to couple light emitted by the lamp 71 into the fiber bundle 77. The light is transported to a location close to the object 9 by the fiber bundle 77 and is emitted from the fiber bundle 77 at an exit end 78 of the bundle 77 and is collimated by collimating optics 79 to provide the illumination light beam 81 directed to the object 9.

The illumination system 63 further comprises a filter plate 83 including an illumination light filter 84 for fluorescence observation and an illumination light filter 85 for normal light observation. An actuator 87 controlled by the controller 35 is provided in order to selectively locate the illumination light filter 84 for fluorescence light observation or the illumination light filter 85 for normal light observation in the beam 74 as indicated by an arrow 88. The illumination light filter 84 for fluorescence light observation is located in the beam 74 if a fluorescence is to be excited in the object to be observed, while the illumination light filter 85 for normal light observation is located in the beam 74 if the object 9 is to be observed under normal light, such as white light. The illumination light filter 85 can be configured such that, for example, it does not allow infrared light or near infrared light generated by the lamp 71 to be transmitted, in order to avoid an unnecessary warming of the object 9, while shorter wavelengths are transmitted.

The selective arrangement of the illumination light filters 84 and 85, respectively, in the beam 74 can be controlled by the user via an input device, such as a button 79.

An observation light filter 91 for fluorescence observation is located in each of the partial beams 15 and 14, wherein an actuator 93 controlled by the controller 35 is provided to selectively remove the observation light filters 91 from the partial beams 14 and 15 as indicated by an arrow 94.

The observation light filters 91 are placed in the beam paths 14, 15 if the illumination light filter 84 for fluorescence observation is arranged in the beam 74, and they are removed from the beam paths 14, 15 if the illumination light filter 85 for normal light observation is arranged in the beam 74. For this purpose, the controller 35 may operate the actuator 93 together with the actuator 87 upon actuation of the input device 97 by the user.

In the illustrated embodiment, the illumination light filter 84 for fluorescence observation and the observation light filter 91 for fluorescence observation are inserted into or removed from the beam path by actuators controlled by the controller. It is, however, also possible that the filters are mounted on filter holders which are directly operated by the hand of the user in order to insert the filters into and remove the filters from the beam paths. The illumination light filter and the observation light filter for fluorescence observation each have transmission characteristics adapted to a fluorescent dye having a fluorescence which is desired to be observed. A plurality of fluorescent dyes are known, and sets of filters including an illumination light filter and an observation light filter can be provided for each of these fluorescent dyes as will be illustrated in more detail below. The fluorescent dyes which can be used with these sets of filters are only limited in that the fluorescence light of these dyes should include wavelength of visible light in order to allow structures of the object 9 containing the fluorescent dye to be perceived with the human eye. Properties of the sets of filters will be illustrated below with reference to an exemplary set of filters including illumination light filters and observation light filters which are designed to observe the fluorescence of the fluorescent dye fluorescein. For this purpose, reference is made to FIGS. 2a to 2d.

Figure 2A:
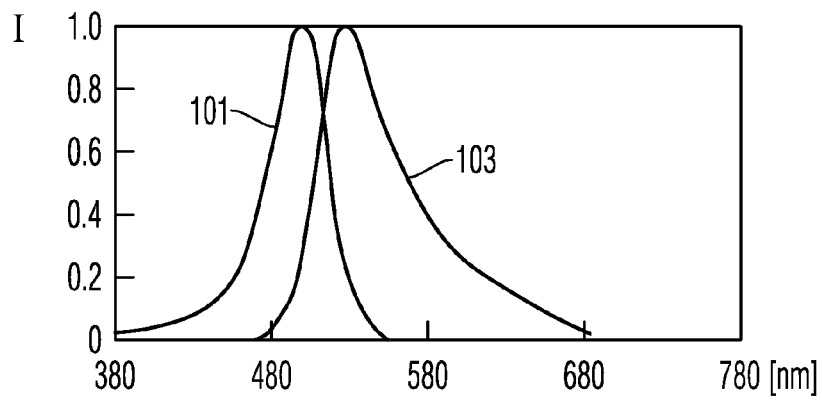
FIGS. 2a to 2d are graphs for schematically illustrating a set of filters for fluorescence observation.

FIG. 2a is a schematic illustration of a graph 101 of the excitation spectrum of fluorescein and a graph 103 of the emission spectrum of fluorescein in a normalized representation. The maximum of the excitation spectrum 101 has a wavelength of about 485 nm, and the maximum of the emission spectrum 103 has a wavelength of about 514 nm, wherein the graphs of the excitation spectrum 101 and of the emission spectrum 103 overlap.

Figure 2B:
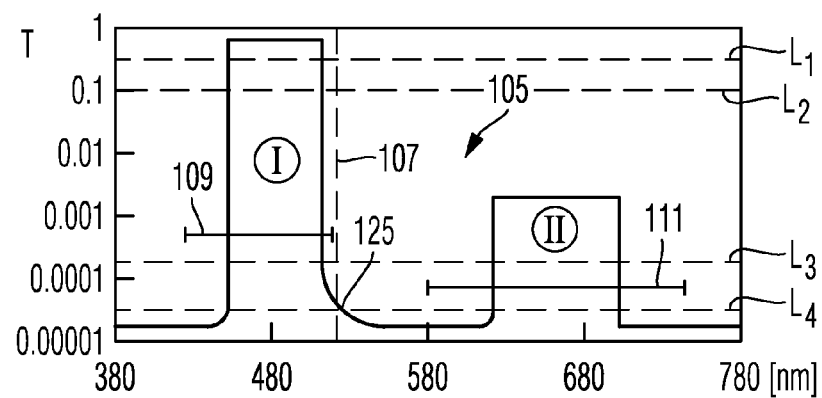

FIG. 2b is a schematic illustration of a graph of a transmission characteristic 105 of the illumination light filter in a logarithmic scale of the ordinate in a wavelength range from 380 nm to 780 nm. This is the wavelength range of visible light relevant for illustrating the properties of the set of filters. The threshold wavelength is designated with reference numeral 107 in FIG. 2b. In the illustrated example, the threshold wavelength 107 is selected such that it is located between the maximum of the excitation spectrum 101 and the maximum of the fluorescence spectrum 103. Such selection is, however, not required. It is also possible to select the threshold wavelength such that it is smaller than the wavelength of the maximum of the excitation spectrum 101 or greater than the wavelength of the maximum of the fluorescence spectrum 103, as long as the excitation spectrum 101 and the fluorescence spectrum 103, respectively, have an intensity value at the threshold wavelength 107 which is significantly greater than zero.

The transmission characteristic 105 is the sum of two partial characteristics I and II defined within the full range from 380 nm to 780 nm. The partial characteristic I has, at wavelengths below the threshold wavelength 107, a wavelength range 109 in which the transmission has values greater than a value L1. The partial characteristic I has a function of allowing fluorescence excitation light to traverse the illumination light filter in order to excite the fluorescence of the fluorescent dye. The transmission of the filter within the wavelength range 109 is selected to be as high as possible in order to achieve a high efficiency. The value L1 represents a transmission value which can be achieved, for example, if the filter is optimized for a high transmission in this wavelength range. In the illustrated example, the value of L1 is 0.6.

The partial characteristic II includes, at wavelengths above the threshold wavelength, at least one second wavelength range in which the transmission has values which are less than a second value L2 and greater than a value L3. The partial characteristic II has a function of allowing light to traverse the illumination light filter which is used for illuminating the object such that its non-fluorescent regions can be perceived rather than for exciting the fluorescence. Since the non-fluorescent regions should not outshine the fluorescent regions and since the fluorescence typically has a low intensity, the illumination light is transmitted with a relatively low intensity by the illumination light filter due to the partial characteristic II. This is the reason why the maximum of the partial characteristic II is less than the value L2 which is smaller than the value L1 which is exceeded by the transmission characteristic in those wavelength ranges in which a transmission as high as possible is desired. The value L2 is 0.1 in the illustrated embodiment. However, the transmission provided by the partial characteristic II is higher than the value L3, which is significantly higher than the value L4. The transmission is below the value L4 within lowest wavelength ranges in which it is desired that the illumination light filter substantially blocks the illumination light. The value L3 is 0.0002 and the value L4 is 0.00005 in the illustrated embodiment.

Figure 2C:
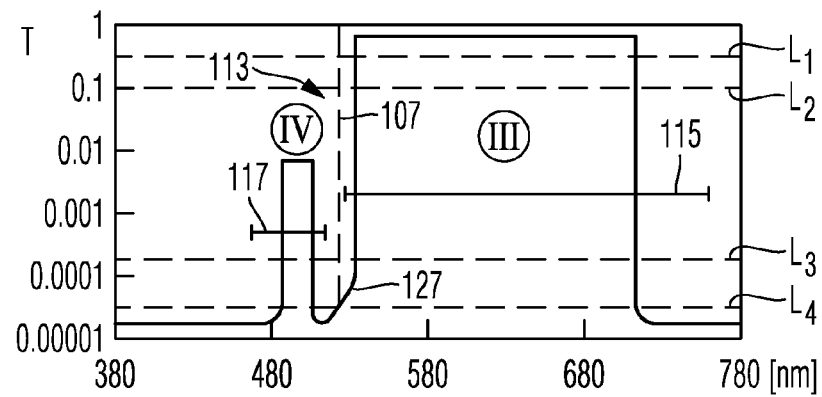

A transmission characteristic 113 of the observation light filter is schematically shown in FIG. 2c. The transmission characteristic 113 is again a sum of two partial characteristics III and IV. The partial characteristic III has, at wavelengths above the threshold wavelength 107, at least one wavelength range 115 in which the transmission has values greater than the value L1. The partial characteristic III has a function of allowing both fluorescence light and illumination light to traverse the observation light filter, which light has reached the object due to the partial characteristic II of the illumination light filter. This is the reason why both fluorescent regions and non-fluorescent regions of the object can be perceived. The fluorescent regions can be perceived since the fluorescent light can traverse the observation light filter due to the partial characteristic III, and the non-fluorescent regions can be perceived since light having reached the object due to the partial characteristic II can traverse the observation light filter.

The partial characteristic IV includes, at wavelengths below the threshold wavelength 107, at least one wavelength range 117 in which the transmission has values which are smaller than the value L2 and greater than the value L3. The partial characteristic IV has a function of allowing light, which reaches the object due to the partial characteristic I of the illumination light filter and which is reflected from or scattered at the object, to traverse the observation light filter in order to make non-fluorescent regions of the object visible. Similar to the partial characteristic II of the illumination light filter, the partial characteristic IV of the observation light filter has maximum transmissions which are smaller than the value L2 and greater than the value L3 in order to avoid outshining of the fluorescent regions. The value L3 is significantly greater than the value L4, wherein the transmission characteristic 113 is below the value L4 in those wavelength ranges in which the transmission of light through the observation light filter should be blocked.

Optical filters having properties as schematically illustrated in FIGS. 2b and 2c can be manufactured, for example, by evaporating multi-layers of dielectric materials on a glass substrate, wherein suitable layer compositions and thicknesses can be determined using mathematical simulation methods as known in the field of optical engineering. Moreover, each of the observation light filter and the illumination light filter can be provided by of two or more separate filters which are together disposed in the optical beam path and provide properties of the whole filter. For example, the illumination light filter may be provided by two suitably selected high pass filters and two suitably selected low pass filters.

Figure 2D:
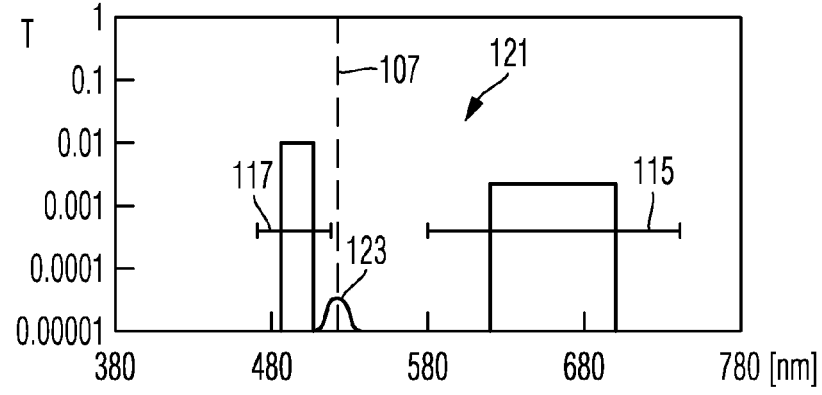

FIG. 2d schematically shows the product of the transmission characteristic 105 of the illumination light filter and the transmission characteristic 113 of the observation light filter. This product shows significant intensities in three wavelength ranges, mainly in the wavelength range 117 in which the partial characteristic IV of the observation light filter is significantly transmitting, in the wavelength range 115 in which the partial characteristic II of the illumination light filter is significantly transmitting, and in a region around the threshold wavelength 107 in which the transmission is represented by a line 123. The transmission represented by the line 123 results from a spectral overlap of a shoulder 125 of the transmission characteristic I and a shoulder 127 of the transmission characteristic III of the observation light filter. It is possible that the shoulders 125 and 127 are intentionally provided in order to provide light for the observation of non-fluorescent regions of the object. It is also possible that the spectral overlap is inevitable in practice since arbitrarily steep edges of the transmission characteristics cannot be achieved due to technical limitations in the manufacture of the filters.

The intensity of the light traversing the set of filters due to the overlap between the shoulders 125 and 127 is $$0 \le \frac{1}{300 \text{ nm}} \int_{400 nm}^{700 nm} T_1(\lambda) \cdot T_3(\lambda) \cdot d\lambda < A_1 \text{ and} \quad (1)$$

and is zero, if no overlap is present, or less than the value $A_1$, if some overlap is present.

The intensity of the light which traverses the set of filters due to the partial characteristic IV in the wavelength range 117 is represented by the formula $$A_1 < \frac{1}{300 \text{ nm}} \int_{400 nm}^{700 nm} T_1(\lambda) \cdot T_4(\lambda) \cdot d\lambda < 0.5 A_2 \quad (2)$$

and is greater than $A_1$ and less than $0.5\ A_2$. Similarly, the intensity which traverses the set of filters due to the partial characteristic II is represented by the formula $$A_1 < \frac{1}{300 \text{ nm}} \int_{400 nm}^{700 nm} T_2(\lambda) \cdot T_3(\lambda) \cdot d\lambda < 0.5 A_2 \quad (3)$$

wherein this intensity is again greater than the intensity caused by the overlap 123 and less than $0.5\ A_2$.

FIG. 2 shows that light from at least two different wavelength ranges significantly contributes to the perception of non-fluorescent regions of the object. This has an advantage in that the non-fluorescent regions of the object do not appear monochrome and that non-fluorescent white regions of the object appear to be nearly white.

The widths and the amounts of the values of the partial characteristic II in the wavelength range 111 and of the partial characteristic IV in the wavelength range 117 define the amounts of light in the various wavelength ranges and are available for observing non-fluorescent regions of the object. In the illustration of FIG. 2d, the available light has a higher spectral power density in the wavelength range from 485 nm to 505 nm due to the partial characteristic IV than in the relatively broader wavelength range from 620 nm to 700 nm due to the partial characteristic II. The spectral distribution of the available light for visualizing non-fluorescent regions of the object is selected such that a non-fluorescent white surface of the object possibly generates a white color impression for the user as illustrated with reference to FIG. 3 below.

Figure 3:
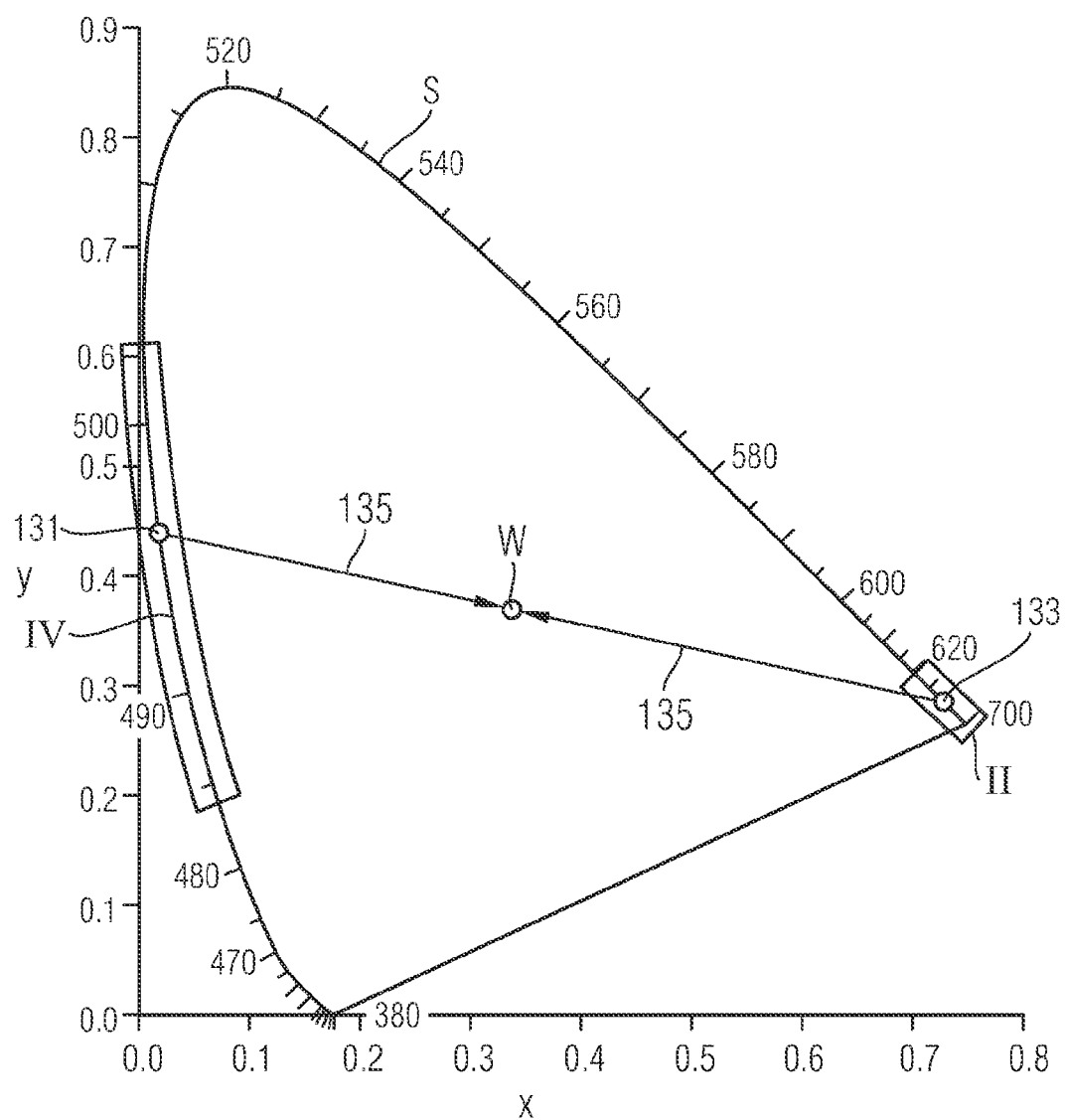
FIG. 3 shows a representation of the chromaticity diagram of the CIE xy chromaticity diagram of the CIE 1931 XYZ color space in which properties of the set of filters illustrated with reference to FIGS. 2a to 2d are shown.

FIG. 3 is a schematic representation of the CIE-chromaticity diagram of the CIE-1931 color space in which the line called the spectral locus carries reference numeral S and in which the white point carries the reference numeral W. A rectangle IV in FIG. 3 designates that region of the spectral locus line S in which the transmission of the partial characteristic IV of the observation light filter has values greater than L3, while a rectangle II designates that region of the spectral locus line S in which the partial characteristic II of the illumination light filter has values greater than L3. Light for observing non-fluorescent regions is provided in the portions II and IV of the spectral locus line, accordingly. A center of gravity of the portion IV is designated by reference numeral 131 in FIG. 3, and a center of gravity of the portion II is designated by reference numeral 133 in FIG. 3. The centers of gravity and weights of the portions IV and II are selected such that the light of these portions adds up to form a mixture of light close to the white point W. This mixing of light is represented in FIG. 3 by arrows 135.

The properties of the transmission characteristics of the illumination light filter and the observation light filter illustrated above are represented by the following formulas (3) and (4):

$$\frac{\int_S T_L(\vec{r}) \cdot T_O(\vec{r}) \cdot \vec{r} \cdot d\vec{r}}{\int_S T_L(\vec{r}) \cdot T_O(\vec{r}) \cdot d\vec{r}} = \vec{R} \text{ and} \quad (3)$$

$$|\vec{W} - \vec{R}| \leq 0.2; \quad (4)$$

wherein:
$\lambda$ designates the wavelength,
$T_L(\lambda)$ is the transmission characteristic of the illumination light filter,
$T_O(\lambda)$ is the transmission characteristic of the observation light filter, and
$\vec{r}$ is a coordinate in CIE xy chromaticity diagram of the CIE 1931 XYZ color space,
S is a line called the spectral locus line in CIE xy chromaticity diagram of the CIE 1931 XYZ color space, and
$\vec{W}$ is the white point in CIE xy chromaticity diagram of the CIE 1931 XYZ color space.

The integral in the enumerator of formula (3) is taken along the spectral locus line S. Due to the term $\vec{r} \cdot d\vec{r}$, a determination of a center of gravity is performed in the coordinates of the color space using a weighting $T_L(\vec{r}) \cdot T_O(\vec{r})$. The integral in the denominator of formula (3) is also taken along the spectral locus line S. This integral is used for normalization such that the value $\vec{R}$ represents the center of gravity of the function $T_L(\vec{r}) \cdot T_O(\vec{r})$ along the spectral line S.

The formula (4) indicates that this center of gravity $\vec{R}$ has a distance from the white point $\vec{W}$ in CIE xy chromaticity diagram of the CIE 1931 XYZ color space of less than 0.2. According to other embodiments, the distance can be less than 0.15 or less than 0.1. This means that the light available for observing a white non-fluorescent object generates a nearly white impression.

The design of the set of filters as illustrated above with reference to FIGS. 2a to 2d has a further advantage in that red light above 620 nm is also available for the observation of non-fluorescent regions due to the partial characteristic II. This allows blood, which may be present on the object, to be perceived with its natural color without disturbing the observation of the fluorescence of the fluorescent dye fluorescein in the green spectral range.

In the context of using the fluorescent dye fluorescein it may be useful to select the threshold wavelength 107 from within a range from 510 nm to 540 nm, and in particular from within a range from 520 nm to 530 nm, to select the wavelength of the wavelength range 111 from within a range from 600 nm to 750 nm, and to select the wavelengths of the wavelength range IV from within a range from 475 nm to 515 nm.

In the context of using the fluorescent dye hypericin, it may be useful to select the threshold wavelength from within a range from 575 nm to 610 nm, and in particular from within a range from 585 nm to 600 nm, to select the wavelength of the wavelength range 111 from within a range from 610 nm to 750 nm, and to select the wavelengths of the wavelength range 117 from within a range from 420 nm to 560 nm. Herein, the wavelength range 117 may in particular comprise two portions, namely a first portion between 420 nm and 490 nm, and a second portion between 510 nm and 560 nm.

In the context of using the fluorescent dye or a precursor of 5ala (protoporphyrin IX), it may be useful to select the threshold wavelength from within a range from 580 nm to 620 nm, to select the wavelength of the wavelength range 111 from within a range from 610 nm to 750 nm, and to select the wavelengths of the wavelength range 117 from within a range from 420 nm to 560 nm. Herein, the wavelength range 117 may in particular comprise two portions, namely a first portion between 420 nm and 490 nm, and a second portion between 510 nm and 560 nm.

The present disclosure illustrates certain exemplary embodiments wherein it is evident that many alternatives, modifications and variations will be apparent to those skilled in the art. Therefore, the exemplary embodiments illustrated in this disclosure are intended to be illustrative and not limiting in any way. Various changes may be made without departing from the spirit and scope of the present disclosure as defined in the following claims.

What is claimed is:

1. A set of filters comprising an illumination light filter and an observation light filter;
   wherein a transmission characteristic of the illumination light filter is a sum of a first partial characteristic and a second partial characteristic;
   wherein a transmission characteristic of the observation light filter comprises at least one third partial characteristic;

wherein the first partial characteristic has, at wavelengths below a threshold wavelength, at least one wavelength range in which the transmission has values greater than a first value;

wherein the second partial characteristic has, at wavelengths above the threshold wavelength, at least one second wavelength range in which the transmission has values less than a second value and greater than a third value, wherein the transmission of the illumination light filter has, between the first wavelength range and the second wavelength range, values less than a fourth value;

wherein the third partial characteristic has, at wavelengths above the threshold wavelength, at least one third wavelength range in which the transmission has values greater than the first value; and wherein the fourth value is less than the third value, the third value is less than the second value and the second value is less than the first value, wherein:

$$\frac{\int_S T_L(\vec{r}) \cdot T_O(\vec{r}) \cdot \vec{r} \cdot dr}{\int_S T_L(\vec{r}) \cdot T_O(\vec{r}) \cdot dr} = \vec{R} \text{ and } |\vec{W} - \vec{R}| \leq 0.15;$$

wherein $\vec{r}$ is a coordinate in the CIE xy chromaticity diagram of the CIE 1931 XYZ color space, S is a line called the spectral locus line of the CIE xy chromaticity diagram of the CIE 1931 XYZ color space, and $\vec{W}$ is the white point in the CIE xy chromaticity diagram of the CIE 1931 XYZ color space.

2. A set of filters comprising an illumination light filter and an observation light filter;

wherein a transmission characteristic of the observation light filter has, at wavelengths below a threshold wavelength, at least one wavelength range in which a transmission has values which are greater than a first value, and the transmission characteristic of the illumination light filter has, at wavelengths above the threshold wavelength, at least one wavelength range in which the transmission has values which are less than a fourth value;

wherein a transmission characteristic of the observation light filter has, at wavelengths above the threshold wavelength, at least one wavelength range in which the transmission has values greater than the first value, and the transmission characteristic of the observation light filter has, below the threshold wavelength, at least one wavelength range in which the transmission has values which are smaller than the fourth value;

wherein $$\frac{\int_S T_L(\vec{r}) \cdot T_O(\vec{r}) \cdot \vec{r} \cdot dr}{\int_S T_L(\vec{r}) \cdot T_O(\vec{r}) \cdot dr} = \vec{R} \text{ and } |\vec{W} - \vec{R}| \leq 0.15;$$

wherein:

$\lambda$ designates the wavelength, $T_L(\lambda)$ is the transmission characteristic of the illumination light filter, $T_O(\lambda)$ is the transmission characteristic of the observation light filter, and $\vec{r}$ is a coordinate in the CIE xy chromaticity diagram of the CIE 1931 XYZ color space, S is a line called the spectral locus in the CIE xy chromaticity diagram of the CIE 1931 XYZ color space, and $\vec{W}$ is the white point in the CIE xy chromaticity diagram of the CIE 1931 XYZ color space.

3. The set of filters according to claim 2, wherein $|\vec{W} - \vec{R}| \leq 0.1$.

4. A fluorescence observation system comprising:

a light source for illuminating an object;

observation optics for imaging the object;

an illumination light filter disposed in an illumination beam path between the light source and the object; and an observation light filter disposed in a beam path of the observation optics;

wherein a transmission characteristic of the observation light filter has, at wavelengths below a threshold wavelength, at least one wavelength range in which a transmission has values which are greater than a first value, and the transmission characteristic of the illumination light filter has, at wavelengths above the threshold wavelength, at least one wavelength range in which the transmission has values which are less than a fourth value;

wherein a transmission characteristic of the observation light filter has, at wavelengths above the threshold wavelength, at least one wavelength range in which the transmission has values greater than the first value, and the transmission characteristic of the observation light filter has, below the threshold wavelength, at least one wavelength range in which the transmission has values which are smaller than the fourth value; and wherein:

$$\frac{\int_S T_L(\vec{r}) \cdot T_O(\vec{r}) \cdot \vec{r} \cdot dr}{\int_S T_L(\vec{r}) \cdot T_O(\vec{r}) \cdot dr} = \vec{R} \text{ and } |\vec{W} - \vec{R}| \leq 0.15;$$

wherein:

$\lambda$ designates the wavelength, $T_L(\lambda)$ is the transmission characteristic of the illumination light filter, $T_O(\lambda)$ is the transmission characteristic of the observation light filter, and $\vec{r}$ is a coordinate in the CIE xy chromaticity diagram of the CIE 1931 XYZ color space, S is a line called the spectral locus in the CIE xy chromaticity diagram of the CIE 1931 XYZ color space, and $\vec{W}$ is the white point in the CIE xy chromaticity diagram of the CIE 1931 XYZ color space.

5. A method of performing a fluorescence observation, wherein the method comprises:

filtering of an illumination light beam directed to an object using an illumination light filter, and filtering of light emanating from the object using an observation light filter;

wherein a transmission characteristic of the observation light filter has, at wavelengths below a threshold wavelength, at least one wavelength range in which a transmission has values which are greater than a first value, and the transmission characteristic of the illumination light filter has, at wavelengths above the threshold wavelength, at least one wavelength range in which the transmission has values which are less than a fourth value;

wherein a transmission characteristic of the observation light filter has, at wavelengths above the threshold wavelength, at least one wavelength range in which the transmission has values greater than the first value, and the transmission characteristic of the observation light filter has, below the threshold wavelength, at least one wavelength range in which the transmission has values which are smaller than the fourth value; and wherein:

$$\frac{\int_S T_L(\vec{r}) \cdot T_O(\vec{r}) \cdot \vec{r} \cdot dr}{\int_S T_L(\vec{r}) \cdot T_O(\vec{r}) \cdot dr} = \vec{R} \text{ and } |\vec{W} - \vec{R}| \leq 0.15;$$

wherein:

$\lambda$ designates the wavelength, $T_L(\lambda)$ is the transmission characteristic of the illumination light filter, $T_O(\lambda)$ is the transmission characteristic of the observation light filter, and $\vec{r}$ is a coordinate in the CIE xy chromaticity diagram of the CIE 1931 XYZ color space, S is a line called the spectral locus in the CIE xy chromaticity diagram of the CIE 1931 XYZ color space, and $\vec{W}$ is the white point in the CIE xy chromaticity diagram of the CIE 1931 XYZ color space.

6. The set of filters according to claim 1, wherein:

$|\vec{W}-\vec{R}|\leq 0.10$.

7. The fluorescence observation system according to claim 4, wherein:

$|\vec{W}-\vec{R}|\leq 0.10$.

8. The method according to claim 5, wherein:

$|\vec{W}-\vec{R}|\leq 0.10$.

* * * * *